United States Patent
Petinarides

(10) Patent No.: US 7,964,017 B2
(45) Date of Patent: Jun. 21, 2011

(54) SYSTEMS AND METHODS FOR CONTROLLING MOISTURE LEVEL IN A GAS

(75) Inventor: John Petinarides, Waxhaw, NC (US)

(73) Assignee: General Dynamics Armament and Technical Products, Inc., Charlotte, NC (US)

( * ) Notice: Subject to any disclaimer, the term of this patent is extended or adjusted under 35 U.S.C. 154(b) by 1239 days.

(21) Appl. No.: 11/418,461

(22) Filed: May 5, 2006

(65) Prior Publication Data

US 2008/0066619 A1  Mar. 20, 2008

(51) Int. Cl.
*B01D 53/02* (2006.01)

(52) U.S. Cl. ............ 95/10; 95/92; 96/108; 96/111; 96/116; 96/243; 96/244; 96/267; 96/399; 96/407; 55/312

(58) Field of Classification Search ............ 96/6, 52, 96/108, 111, 116, 243, 244, 267, 399, 407; 95/10, 92; 55/312
See application file for complete search history.

(56) References Cited

U.S. PATENT DOCUMENTS

| | | | |
|---|---|---|---|
| 3,976,450 A | 8/1976 | Marcote et al. | |
| 4,019,863 A | 4/1977 | Jenkins et al. | |
| 4,906,257 A | 3/1990 | Fukanaga | |
| 5,639,956 A | 6/1997 | Christy | |
| 5,723,861 A * | 3/1998 | Carnahan et al. | 250/287 |
| 6,418,965 B2 | 7/2002 | Bryselbout | |
| 6,495,823 B1 | 12/2002 | Miller et al. | |

(Continued)

FOREIGN PATENT DOCUMENTS

DE  102005018142  10/2006

(Continued)

OTHER PUBLICATIONS

"Differential Mobility Spectrometry: The Technology Of Choice For Miniaturized, High Performance, Fieldable Chemical And Biological Detection Systems", ECE 500: ECE Seminar—Raanan Miller, Graduate Seminar, http://www.ece.uiuc.edu/seminar/05-06/dec01-05-miller.html, Dec. 1, 2005, (2 pages).

(Continued)

*Primary Examiner* — Duane Smith
*Assistant Examiner* — Tiffany N Palmer
(74) *Attorney, Agent, or Firm* — Hunton & Williams

(57) ABSTRACT

A gas flow system and method are provided for controlling the moisture in a gas flow. The system may include a gas source from which gas flows, a processing chamber to which the gas flows, and a gas flow line through which the gas flows from the gas source to the processing chamber. The gas flow line may include a moisture control line section. The moisture control line section includes a pass-through line through which the gas may pass, so as to be exposed to a dryer. The exposure to a dryer may be controlled by a suitable valve. A scrubber is disposed in the gas flow line, the scrubber removing contaminates from the gas in the gas flow. The system may include a moisture sensor disposed in the gas flow, the moisture sensor sensing at least one parameter of the gas and outputting a signal representing the at least parameter to a moisture sensor controller, such that the moisture sensor controller determines the moisture in the gas. The moisture sensor controller controls the flow of the gas so as to control the moisture in the gas by adjusting the valve.

20 Claims, 4 Drawing Sheets

U.S. PATENT DOCUMENTS

| | | | |
|---|---|---|---|
| 6,512,224 B1 | 1/2003 | Miller et al. | |
| 6,690,004 B2 | 2/2004 | Miller et al. | |
| 6,727,496 B2 | 4/2004 | Miller et al. | |
| 6,806,463 B2 | 10/2004 | Miller et al. | |
| 6,809,313 B1 | 10/2004 | Gresham et al. | |
| 6,815,668 B2 | 11/2004 | Miller et al. | |
| 6,815,669 B1 | 11/2004 | Miller et al. | |
| 6,948,929 B2 | 9/2005 | Komai | |
| 6,972,407 B2 | 12/2005 | Miller et al. | |
| 7,005,632 B2 | 2/2006 | Miller et al. | |
| 7,030,372 B2 | 4/2006 | Miller | |
| 7,318,858 B2 | 1/2008 | Parsa | |
| 2001/0049998 A1 | 12/2001 | Rode | |
| 2002/0139245 A1* | 10/2002 | Kesten et al. | 95/52 |
| 2005/0092914 A1 | 5/2005 | Miller et al. | |
| 2005/0156107 A1 | 7/2005 | Miller et al. | |
| 2006/0100744 A1* | 5/2006 | Sharma et al. | 700/276 |
| 2007/0228269 A1 | 10/2007 | Miller et al. | |
| 2008/0282772 A1 | 11/2008 | Petinarides | |

FOREIGN PATENT DOCUMENTS

WO    WO 2006/110700    10/2006

OTHER PUBLICATIONS

Notification of Transmittal of the International Search Report and the Written Opinion of the International Searching Authority, or the Declaration, dated Feb. 25, 2009.

Notification of Transmittal of the International Search Report and the Written Opinion of the International Searching Authority, or the Declaration, dated Mar. 6, 2009.

Notification of Transmittal of the International Search Report and the Written Opinion of the International Searching Authority, or the Declaration, dated Feb. 20, 2009.

Yang, Ralph T., "Absorbents: Fundamentals and Applications," Wiley Online Library http//onlinelibrary.wiley.com/book/10.1002/047144409X Jun. 2003 (1 page).

Knaebel, K.S., "Adsorbent Selection," Adsorption Research Inc., http//www.adsorption.com/publications.AdsorbentSel1B.pdf, Jun. 2004 (24 pages).

GB0708425.4, UK Search Report dated Aug. 28, 2007.

\* cited by examiner

SYSTEMS AND METHODS FOR CONTROLLING MOISTURE LEVEL IN A GAS

BACKGROUND OF THE INVENTION

The invention is directed to a system and method for controlling a moisture level in a gas, and in particular to controlling the moisture level in a circulating gas flow.

There are a variety of systems which utilize a flowing gas, such as a circulating gas. Such a system includes a Differential Mobility Spectrometer (DMS) system, for example. In some of such systems, it is desired or needed to control the moisture level in the flowing gas. There are known systems for controlling the moisture level in flowing gases. However, known systems fail to provide an arrangement by which the moisture may be controlled in an efficient and effective manner. The invention provides such a system.

BRIEF SUMMARY OF THE INVENTION

A gas flow system and method are provided for controlling the moisture in a gas flow. The system may include a gas source from which gas flows, a processing chamber to which the gas flows, and a gas flow line through which the gas flows from the gas source to the processing chamber. The gas flow line may include a moisture control line section. The moisture control line section includes a pass-through line through which the gas may pass, so as to be exposed to a dryer. The exposure to a dryer may be controlled by a suitable valve. A scrubber is disposed in the gas flow line, for example outside of the moisture control line section. The scrubber removes contaminates from the gas in the gas flow. The system may include a moisture sensor disposed in the gas flow, the moisture sensor sensing at least one parameter of the gas and outputting a signal representing the at least parameter to a moisture sensor controller, such that the moisture sensor controller determines the moisture in the gas. The moisture sensor controller controls the flow of the gas so as to control the moisture in the gas by adjusting the valve.

BRIEF DESCRIPTION OF THE DRAWINGS

The present invention can be more fully understood by reading the following detailed description together with the accompanying drawings, in which like reference indicators are used to designate like elements, and in which.

DETAILED DESCRIPTION OF THE INVENTION

Hereinafter, aspects of a moisture control system in accordance with various embodiments of the invention will be described. As used herein, any term in the singular may be interpreted to be in the plural, and alternatively, any term in the plural may be interpreted to be in the singular.

The systems and methods described herein provide an approach to control the moisture level in a flowing gas. In accordance with one embodiment of the invention, the invention may be used in conjunction with a DMS (Differential Mobility Spectrometry) system. Such a system is described in U.S. Pat. No. 7,030,372, which is incorporated herein by reference in its entirety. That is, a DMS system, as well as other systems, utilize a flowing gas, i.e., such as a carrier gas. However, the performance and operation of such systems may depend on the moisture level of such gas being maintained at a particular level. The invention provides a novel approach to maintain the moisture level in a flowing gas at a particular moisture level, or at least control the moisture to be close to a particular level.

In accordance with one embodiment of the invention, the invention may be used in conjunction with a DMS system, i.e., to control the moisture level of a carrier gas in a DMS system. However, the systems and methods of embodiments are not limited to such implementation. That is, embodiments may be utilized in any system in which it is desired or needed to control the moisture level in a flowing gas.

Figure 1:
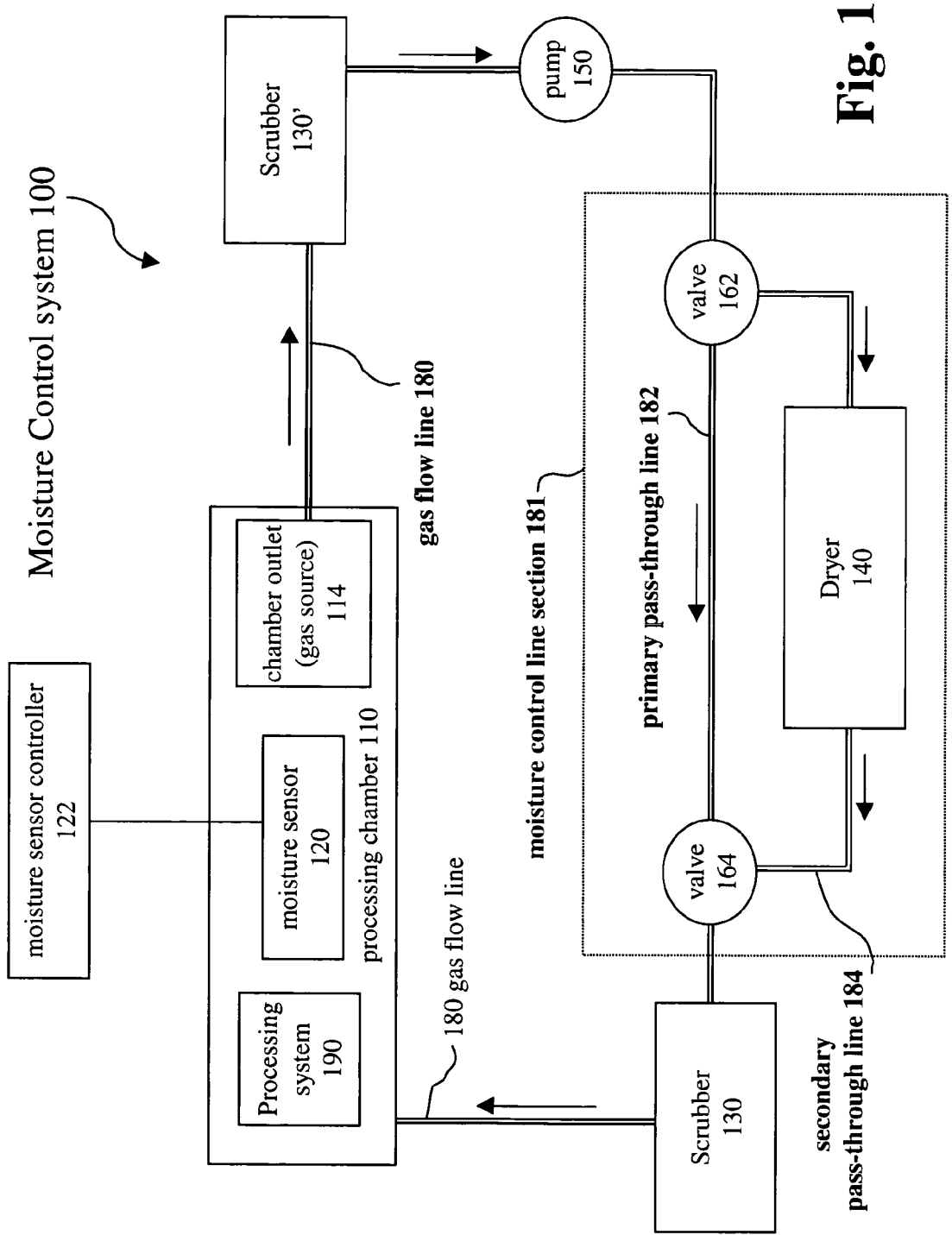
FIG. 1 is a block diagram of a moisture control system with a re-circulating gas flow in accordance with one embodiment of the invention.

FIG. 1 is a block diagram of a moisture control system 100 in accordance with one embodiment of the invention. As shown, the moisture control system 100 includes a processing chamber 110. The processing chamber 110 includes a processing system 190. The processing system 190 performs the particular processing desired. That is, the processing system 190 may perform DMS processing or any other processing that the provided system 190 is intended to provide. The processing system 190, however, requires that the moisture or moisture content of the gas passing through the processing chamber 110 be controlled. For example, the processing system 190 may require that the moisture content of the gas in the processing chamber 110 be within a particular range, i.e., not to exceed a first value, nor fall below a second value. The arrangement of the invention provides such capability.

That is, the moisture control system 100 includes a moisture sensor 120, in conjunction with a moisture sensor controller 122. The moisture sensor 120 is suitably disposed in the gas flow. For example, the moisture sensor 120 may be disposed in the processing chamber 110. The moisture sensor 120 senses at least one parameter of the gas and outputs a signal representing the at least parameter to a moisture sensor controller 122. The moisture sensor controller 122 analysis the parameter or parameters to determine the moisture content of the gas. Any known sensor may be utilized to collect data suitable for ascertaining the moisture content in the gas. The moisture content or moisture level is adjusted based on the moisture sensed by the moisture sensor 120, as described hereinafter.

The moisture control system 100 includes a gas flow line 180. Gas passes out of the processing chamber 110 through a chamber outlet 114 and into the gas flow line 180. As shown in FIG. 1, the gas repeatedly circulates through the gas flow line 180 in a closed loop manner, in accordance with one embodiment of the invention. That is, the gas passes out of the chamber outlet 114 into the gas flow line 180, passes through various components disposed along the gas flow line 180, and then passes back into the processing chamber 110. During such circulation, the moisture in the gas is controlled. A pump 150 is used to pump the gas through the gas flow line 280.

The moisture control system 100 includes at least one scrubber (130, 130') as shown in FIG. 1. A scrubber or scrubbers are provided to remove contaminates from the circulating gas. The scrubber 130 may be disposed in the gas flow line 180 as desired. For example, a scrubber 130' may be disposed immediately after the gas exits the processing chamber 110 and/or a scrubber 130 may be disposed immediately before the gas enters the processing chamber 110.

As disclosed herein, a "scrubber" is described as any medium or substance capable of removing contaminates from the gas. The primary purpose of a scrubber as described herein is to remove such contaminates, and not to remove moisture from the gas. This is in contrast to a "dryer" as disclosed herein, which the primary purpose of is to remove moisture from the gas.

Accordingly, a scrubber may be described as any medium/substance (such as activated charcoal) capable of removing analytes and other contaminating materials from the gas. In particular, in one embodiment, scrubbers may be provided to remove analytes or contaminating vapors from the carrier gas (used to transport ions through an analytical region of a differential mobility spectrometer) in a spectrometer, i.e., in a DMS system. It is expected that any such scrubber material will have some capacity to absorb moisture. However, in the applications of the moisture control system 100, it may be advantageous to use a scrubber material with a relatively low saturation point for moisture absorption. This characteristic is useful in being able to condition the scrubber to a specific level of moisture, capable of maintaining the carrier gas or other gas to within a range of moisture content, required for the optimal performance of the spectrometer or other processing system 190.

The moisture control system 100 also includes a dryer 140. As disclosed herein, a "dryer" is described as any medium or substance capable of removing moisture from the gas. The primary purpose of a dryer, as described herein, is to remove moisture, and not to remove contaminates from the gas. This is in contrast to a "scrubber" as disclosed herein, which the primary purpose of is to remove contaminates from the gas.

In accordance with one embodiment of the invention, a dryer includes a drying agent. The dryer agent may be described as any material or desiccant capable of removing moisture from the gas, e.g. air or carrier gas used in a spectrometer. A molecular sieve, as is well known in the art, is a very efficient dryer and is capable of binding water molecules to itself and not releasing it back to the carrier gas until it reaches a high saturation point. This characteristic makes it ideally suited to its function in the moisture control system 100 where it is used to take out excess moisture from the gas and thus maintain the required moisture level for the gas. It is recognized that a molecular sieve, or other dryer that is utilized, may also remove some contaminants. However contaminant removal is not required for the dryer material.

As shown in FIG. 1, the gas flow line 180 includes a moisture control line section 181. As shown, the moisture control line section 181 is a section of the gas flow line 180. The moisture control line section 181 includes a primary pass-through line 182 and a secondary pass-through line 184. The secondary pass-through line 184 includes a dryer 140, whereas the primary pass-through line 182 does not. As shown, the primary pass-through line 182 and the secondary pass-through line 184 are disposed in parallel to each other. In accordance with one embodiment of the invention, the gas is controlled to flow through either the primary pass-through line 182 or the secondary pass-through line 184, i.e., the gas flow is switched back and forth between the two pass-through lines (182, 184).

A pair of dryer valves (162, 164) may be provided to control which pass-through line (182, 184) the gas passes. That is, the dryer valves may include a first valve 162 and a second valve 164. The first valve 162 selectably controls the gas flow to pass into the primary pass-through line 182 or the secondary pass-through line 184. The second valve 164 selectably controls the gas flow to exit from the primary pass-through line 182 or the secondary pass-through line 184. Accordingly, in accordance with this embodiment of the invention, the dryer valves (162, 164) are controlled together to control whether the gas flows through the primary pass-through line 182 or the secondary pass-through line 184.

Specifically, the dryer valves (162, 164) are controlled by the moisture sensor controller 122. As described above, the moisture sensor 120, disposed in the gas flow, senses at least one parameter of the gas and outputs this information to the moisture sensor controller 122. The at least one parameter provides the data to the moisture sensor controller 122 by which the moisture sensor controller 122 may determine the moisture content of the gas. Based on the determination of the moisture in the gas, the moisture sensor controller 122 switches the valves (162, 164) so that the gas flows through either the primary pass-through line 182 or the secondary pass-through line 184.

In accordance with one embodiment of the invention, the moisture sensor controller 122 may maintain the moisture between an upper and a lower threshold value as desired, i.e., within a moisture range defined by a first threshold value and a second threshold value. It is of course appreciated that the particular range will depend on the needs of the particular processing system 190.

Accordingly, the moisture sensor controller 122 may be provided to switch the gas flow from the primary pass-through line 182 to the secondary pass-through line 184 upon exceeding a first threshold value, i.e., upon the moisture content getting equal to or above a certain value. That is, once the first threshold value is attained, the moisture sensor controller 122 switches the valves (162, 164) to switch the gas flow from the primary pass-through line 182 to the secondary pass-through line 184. As a result, the gas flow will be directed through the dryer 140 in the secondary pass-through line 184. Over time, the dryer will dry the gas and the moisture content in the gas will drop.

Once the moisture content in the gas has dropped a sufficient amount, a second threshold value will be attained or exceeded. Once this occurrence has been identified, the moisture sensor controller 122 switches the valves (162, 164) so as to switch the flow back through the primary pass-through line 182. That is, the gas has been dried sufficiently and further drying is not desired. In accordance with one embodiment of the invention, the primary pass-through line 182 may simply be an uninterrupted line extending from the valve 162 to the valve 164. Accordingly, minimal if any drying takes place in the primary pass-through line 182.

As shown in FIG. 1, gas passes out of the processing chamber 110 via a chamber outlet 114. Accordingly, the chamber outlet 114 might be thought of as the being the beginning of the circulation of the gas, or alternatively, as the gas source. In the closed loop system of FIG. 1, the gas circulates through the gas flow line 180, into the processing chamber 110 and subsequently again exits the processing chamber 110 via the chamber outlet 114. However, the invention is not limited to such arrangement as shown in FIG. 1.

Figure 2:
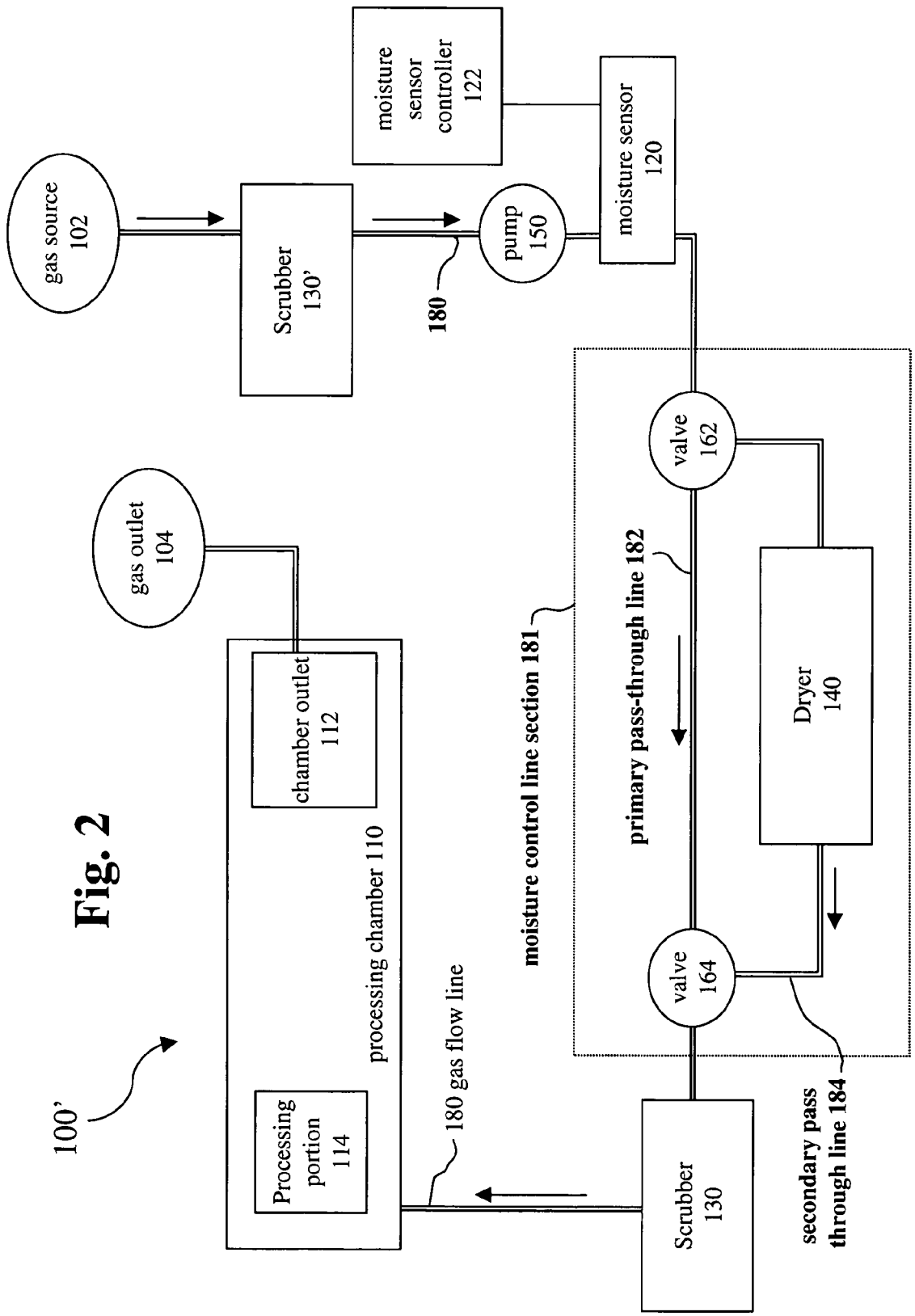
FIG. 2 is a further block diagram of a moisture control system with a non re-circulating gas flow in accordance with one embodiment of the invention.

That is, FIG. 2 shows an alternative arrangement of a moisture control system 100'. As discussed above, the moisture control system 100' includes scrubbers (130, 130'), a pump 150, a moisture control line section 181, and a processing chamber 110. However, in the moisture control system 100' of FIG. 2, the gas does not circulate in a closed loop fashion. Rather, the gas flows from a gas source 102, through the gas flow line 180, into the processing chamber 110. Thereafter, the gas flows out of the processing chamber 110, via the chamber outlet 112, and into a gas outlet 104. Once the gas passes through the gas outlet 104, the gas is expelled from the system, i.e., and is not re-circulated.

In the arrangement of FIG. 2, the moisture sensor 120 is disposed upstream of the moisture control line section 181, i.e., between the gas source 102 and the moisture control line section 181. Accordingly, the moisture sensor 120, working with the moisture sensor controller 122, senses the moisture of the gas prior to passing through the moisture control line section 181. Depending on the sensed moisture, the moisture sensor controller 122 of FIG. 2 selectively switches the gas flow from the primary pass-through line 182 to the secondary pass-through line 184 to reduce the moisture in the gas (or switches the flow from the secondary pass-through line 184 to the primary pass-through line 182 if the moisture content falls below a particular value). Alternatively, the moisture sensor 120 of FIG. 2 might be disposed in the processing chamber 110.

It is appreciated that in the embodiment of FIG. 2, as well as in the other embodiments, the invention is not limited to just one moisture sensor 120. Rather, two or more moisture sensors 120 might be used to effectively monitor and control the moisture in the gas. For example, in the arrangement of FIG. 2, a moisture sensor 120 might be also be placed downstream from the moisture control line section 181, e.g. such as in the processing chamber 110. In any case, placement of the moisture sensors 120 may be provided to allow a desired moisture content to be attained in the processing chamber 110, hand in hand with making appropriate adjustments for changes in moisture content of the incoming gas, i.e., flowing from the gas source 102.

Figure 3:
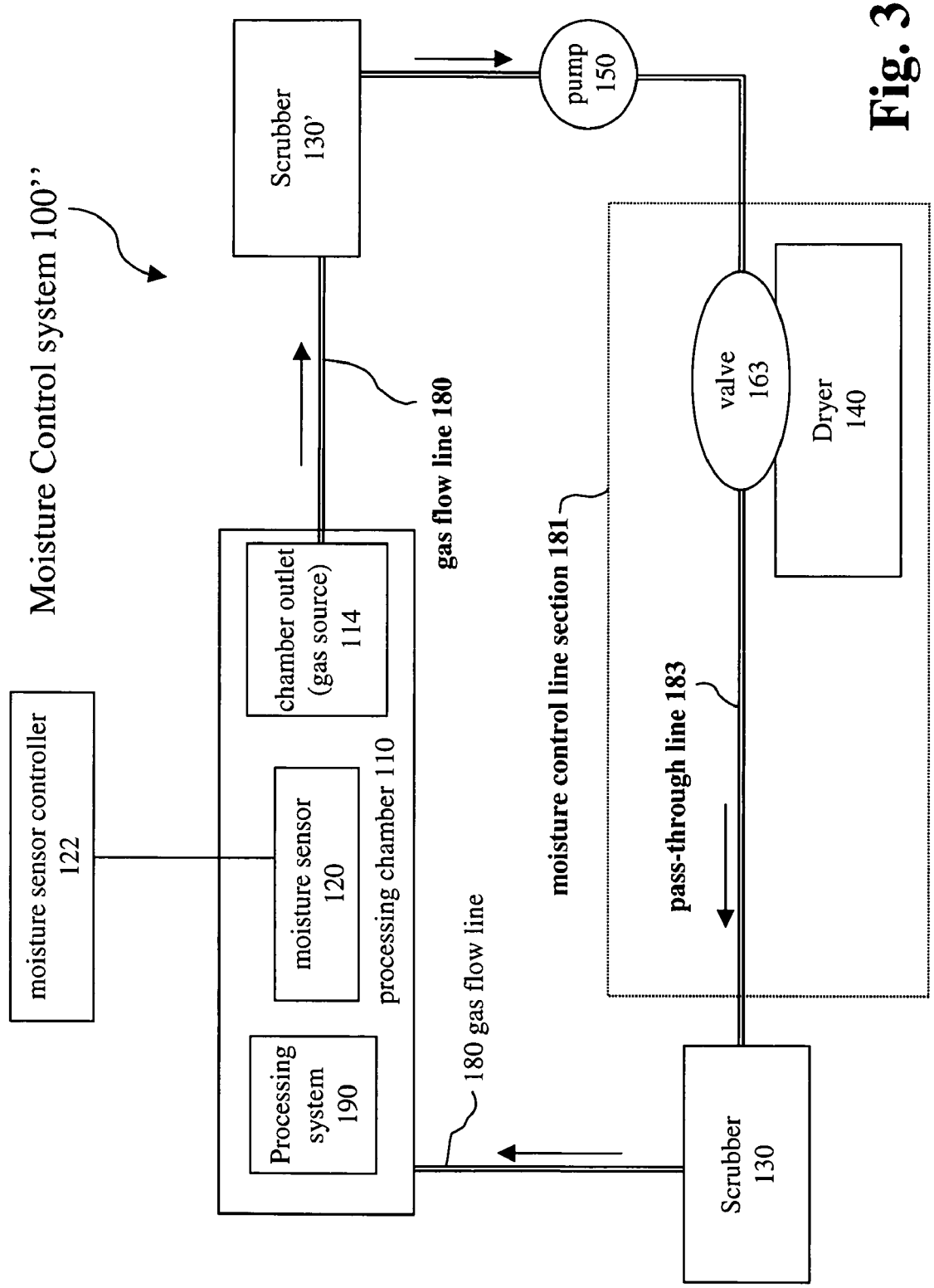
FIG. 3 is a further block diagram of a moisture control system utilizing an alternative dryer arrangement in accordance with one embodiment of the invention.

FIG. 3 is a block diagram of a moisture control system 100" in accordance with a further embodiment of the invention. As shown, various components of the moisture control system 100" are the same as described above with reference to FIG. 1. However, in the arrangement of FIG. 3, the gas flow line 180 includes only a single pass-through line 183, in the moisture control line section 181. The moisture control line section 181 further includes a single valve 163. The moisture control line section 181 further includes a dryer 140. The dryer 140 of FIG. 3 might be in form of a compartment of a molecular sieve, for example.

In accordance with this embodiment of the invention shown in FIG. 3, when the gas starts to get wetter than desired, this information will be output from the moisture sensor 120 to the moisture sensor controller 122. In response, the moisture sensor controller 122 will open up the valve 163 so as to expose the gas passing through the pass-through line 183 to the dryer 140. Through diffusion of the passing gas into the dryer 140, the gas will be dried over time.

Once the gas is dried to a desired degree, this information will be conveyed to the moisture sensor controller 122 from the moisture sensor 120. At that point, the moisture sensor controller 122 will close the valve 163, thus cutting off the circulation/diffusion of the gas into the dryer 140. As can be appreciated, once the gas, over time, again gets wetter than desired, the moisture sensor controller 122 will again open the valve 163, and so forth. In this manner, the moisture content of the gas in the moisture control system 100" is monitored and controlled.

Figure 4:
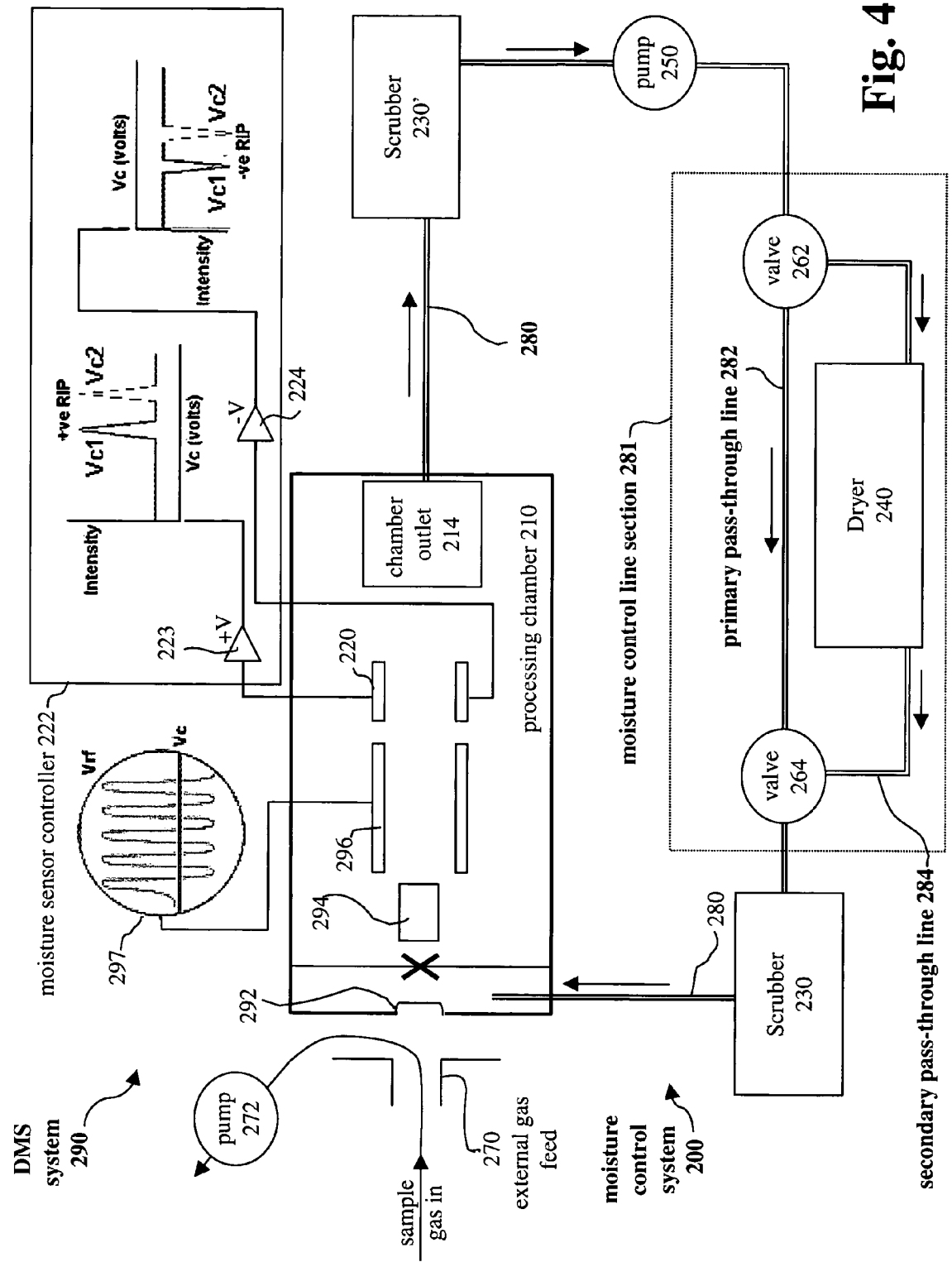
FIG. 4 is a further block diagram of a moisture control system in conjunction with a DMS system in accordance with one embodiment of the invention.

FIG. 4 is a block diagram in accordance with a further embodiment of the invention. In particular, FIG. 4 shows implementation of the moisture control system 200 in conjunction with a DMS system 290.

The moisture control system 200 is similar in many ways to the moisture control system 100 described above. However, the system 200 of FIG. 4 is utilized to monitor a carrier gas in a DMS system. Accordingly, the moisture control system 200 of FIG. 4 includes a processing chamber 210 and scrubbers (230, 230'). A pump 250 is used to pump the gas through the gas flow line 280.

As described above, a gas flow line 280 includes a moisture control line section 281. The moisture control line section 281 includes a primary pass-through line 282 and a secondary pass-through line 284. The secondary pass-through line 284 includes a dryer (through which the flow may be diverted upon the gas getting wet enough). Valves (262, 264) selectively control the flow of gas through either the primary pass-through line 282 or the secondary pass-through line 284. The valves (262, 264) are controlled by the moisture sensor controller 222.

Hereinafter, further aspects of the DMS ((Differential Mobility Spectrometry) will be described. DMS technology is also known as FIS (Field Ion Spectrometry) and FAIMS (Field Asymmetric Ion Mobility Spectrometry). The DMS system as shown in FIG. 4 requires a clean recirculating carrier gas that provides optimal detection performance at specific moisture levels in the carrier gas.

The arrangement of FIG. 4 includes both a DMS system 290 and a moisture control system 200, i.e., which supports that DMS system. The DMS system 290 includes a sample membrane 292, a spectrometer 294 and analytical plates 296. Output of the DMS includes spectral information 297, as is known in the art.

It has been demonstrated that DMS technology may be optimized between being highly sensitive and highly selective by holding the carrier gas at a particular moisture level. A molecular sieve is a very efficient dryer and scrubber (cleaner) of the carrier gas but may not be efficiently used to condition the gas at a particular moisture level. On the other hand, activated charcoal is a very efficient scrubber of carrier gas but not very efficient at drying. Accordingly, one idea behind an embodiment of the invention is to use activated charcoal as the "scrubber" 230 and a molecular sieve as the "dryer" 240 to control the moisture level.

The DMS system 290 is provided with sample gas using an external gas feed 270. The external gas feed 270 may utilize a pump 272 to move the sample gas past the sample membrane 292, or may provide the sample gas in any other suitable manner. During operation of the DMS system 290, the carrier gas flowing through the gas flow line 280 gets wetter. This is typically primarily due to moisture permeating through the sample membrane 292. As described herein, as the gas gets wetter, the RIP moves and as it approaches Vc1 the dryer controller switches the two 3 way latching valves (262, 264), to divert the carrier gas through the dryer 240, e.g. which may be in the form of a molecular sieve dryer.

As shown in FIG. 4, the system uses valves (262, 264), i.e., such as two (2) three way valves, to switch the molecular sieve (dryer) 240 from a sealed non active mode to an active mode in series with the recirculating carrier gas. In accordance with one embodiment of the invention, small amounts of molecular sieve may be added to the activated charcoal (e.g. the scrubbers (230, 230')) to remove contamination.

In accordance with this embodiment of the invention, the output of the DMS system 290 provides spectral information 297 on the carrier gas by way of the Reactant Ion Peak (RIP), as is known in the art. Further, at a particular temperature and pressure (maintained at a constant value), the Reactant Ion Peak (RIP) provides an accurate indication of the moisture level. The position of the RIP (at a fixed Vrf) is identified by the value of the "compensation voltage" Vc. This information is used by the moisture sensor controller 222 to control the dryer valves (262, 264) and thus the level of moisture in the carrier gas. As shown in FIG. 4, the moisture sensor controller 222 may include amplifiers (223, 224)

On initial set up of the DMS system, the gas management system may be conditioned to a particular moisture level of the carrier gas, except for the dryer compartment 240 (with molecular sieve) which is conditioned to be as dry as possible. The dryer control system is set to control the moisture level in the carrier gas at between an upper and lower level, as represented by RIP positions Vc1 and Vc2.

As the carrier gas gets wetter, primarily through moisture permeating through the sample membrane, the RIP moves and as it approaches Vc1 the dryer controller 222 switches the two 3 way latching valves, to divert the carrier gas through the molecular sieve dryer. As the molecular sieve dryer starts to dry the carrier gas, the RIP position will move towards Vc2 and the dryer controller will operate the two 3 way latching valves to set the gas system back to normal operation (dryer off). Because of hysteresis in the wetting and drying part of the control cycle, it should be appreciated that the actual switching points are somewhere between Vc1 Vc2.

As described above, the moisture control system of embodiments include various pumps to pump the gas, e.g. carrier gas, through the moisture control system. It is appreciated that any suitable pump arrangement may be used. Alternatively, the gas might be passed through the gas flow line in any other suitable manner.

Further, in the embodiments described above, various valves are used. It is appreciated that any suitable valve may be used. For example, a three way latch valve might be used, or any other suitable valve.

It will be readily understood by those persons skilled in the art that the present invention is susceptible to broad utility and application. Many embodiments and adaptations of the present invention other than those herein described, as well as many variations, modifications and equivalent arrangements, will be apparent from or reasonably suggested by the present invention and foregoing description thereof, without departing from the substance or scope of the invention.

Accordingly, while the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications and equivalent arrangements.

What is claimed is:

1. A gas flow system for controlling the moisture in a gas flow, the system comprising:
    a gas source from which gas flows;
    a processing chamber to which the gas flows;
    a gas flow line through which the gas flows from the gas source to the processing chamber, the gas flow line including a moisture control line section, the moisture control line section including:
        a primary pass-through line;
        a secondary pass-through line, the primary pass-through line disposed such that flow of the gas through the primary pass-through line is in parallel to flow through the secondary pass-through line, and such that the gas flows through either the primary pass-through line or the secondary pass-through line, and the drying characteristics of the secondary pass-through line being different than the drying characteristics of the primary pass-through line;
        a dryer, the dryer disposed in the secondary pass-through line, the dryer effecting the drying characteristics of the secondary pass-through line being different than the drying characteristics of the primary pass-through line; and
        dryer valves, the dryer valves including:
            a first valve, the first valve selectably controlling the gas flow to pass into either the primary pass-through line or the secondary pass-through line such that the gas is controlled to flow through either the a primary pass-through line or the secondary pass-through line; and
            a second valve, the second valve selectably controlling the gas flow to exit from either the primary pass-through line or the secondary pass-through line;
    a scrubber disposed in the gas flow line outside of the moisture control line section, the scrubber removing contaminates from the gas in the gas flow; and
    a moisture sensor disposed in the gas flow, the moisture sensor sensing at least one parameter of the gas and outputting a signal representing the at least parameter to a moisture sensor controller such that the moisture sensor controller determines the moisture in the gas, the moisture sensor controller selectably controlling, based on the moisture, flow of the gas through either the primary pass-through line or the secondary pass-through line, the moisture sensor controller so controlling the moisture in the gas by adjusting the dryer valves.

2. The gas flow system of claim 1, wherein the scrubber is disposed downstream in the gas flow from the moisture control line section.

3. The gas flow system of claim 1, wherein the dryer is a molecular sieve.

4. The gas flow system of claim 1, wherein the scrubber is a first scrubber disposed downstream in the gas flow from the moisture control line section, the system further including a second scrubber, the second being disposed upstream from the moisture control line section.

5. The gas flow system of claim 1, the system further including a pump that pumps the gas through the gas flow line.

6. The gas flow system of claim 5, wherein the pump is disposed upstream from the moisture control line section.

7. The gas flow system of claim 1, the moisture sensor disposed in the processing chamber.

8. The gas flow system of claim 1, wherein the system further includes a chamber outlet, the chamber outlet disposed in the processing chamber, and the chamber outlet constituting the gas source, such that the gas flow is a re-circulating gas flow.

9. The gas flow system of claim 1, wherein the gas flow is a non-circulating gas flow, such that the gas passes from the gas source to the processing chamber and thereafter out of the gas flow system and does not re-circulate back through the gas source.

10. The gas flow system of claim 1, wherein each of the first valve and the second valve is a three-way latch valve.

11. The gas flow system of claim 1, wherein the primary pass-through line does not include a dryer.

12. The gas flow system of claim 1, wherein the moisture control line section does not include a scrubber.

13. The gas flow system of claim 1, wherein the scrubber includes charcoal.

14. The gas flow system of claim 1, wherein the system is part of a differential mobility spectrometry system.

15. The gas flow system of claim 1, wherein the signal is a voltage.

16. The gas flow system of claim 1, wherein the moisture sensor controller:
   switches the gas flow from the primary pass-through line to the secondary pass-through line upon exceeding a first threshold value; and
   switches the gas flow from the secondary pass-through line to the primary pass-through line upon falling below a second threshold value.

17. A gas flow system for controlling the moisture in a gas flow, the system comprising:
   a gas source from which gas flows;
   a processing chamber to which the gas flows;
   a gas flow line through which the gas flows from the gas source to the processing chamber, the gas flow line including a moisture control line section, the moisture control line section including a pass-through line;
   a dryer compartment disposed adjacent the pass-through line with a dryer disposed in the dryer compartment;
   a dryer valve that is selectively opened such that gas in the pass-through line is allowed to pass into the dryer compartment, or that is closed to selectively close the dryer compartment from the pass-through line such that the gas passes around the dryer compartment, and the dryer effecting drying characteristics of the gas that passes through the dryer compartment to be different than gas that passes around the dryer compartment;
   a scrubber disposed in the gas flow line, the scrubber removing contaminates from the gas in the gas flow;
   a moisture sensor disposed in the gas flow, the moisture sensor sensing at least one parameter of the gas and outputting a signal representing the at least parameter to a moisture sensor controller, the moisture sensor controller controlling the opening or closing of the dryer valve, thereby controlling the moisture content in the gas.

18. A method for controlling the moisture in a processing chamber, the method including:
   circulating gas through a gas flow line through which the gas flows from a gas source to the processing chamber, the gas flow line including a moisture control line section, the moisture control line section including:
      a primary pass-through line;
      a secondary pass-through line, the primary pass-through line disposed such that flow of the gas through the primary pass-through line is in parallel to flow through the secondary pass-through line such that the gas selectively flows through either the primary pass-through line or the secondary pass-through line, the drying characteristics of the secondary pass-through line being different than the drying characteristics of the primary pass-through line, and dryer disposed in the secondary pass-through line, the dryer effecting the drying characteristics of the secondary pass-through line being different than the drying characteristics of the primary pass-through line;
   monitoring the moisture of the gas in the gas flow line;
   controlling the moisture in the gas, based on observed moisture in the gas, by controlling whether the gas passes through the primary pass-through line, or alternatively, the secondary pass-through line;
   scrubbing the gas using a scrubber, the scrubber removing contaminates from the gas in the gas flow.

19. The method of claim 18, wherein the monitoring the moisture of the gas in the gas flow line is performed using a moisture sensor disposed in the processing chamber.

20. The method of claim 18, wherein the scrubber is disposed in the gas flow line outside of the moisture control line section.

* * * * *